(12) United States Patent
Lu et al.

(10) Patent No.: US 11,135,004 B2
(45) Date of Patent: Oct. 5, 2021

(54) ABLATION DEVICE

(71) Applicant: Industrial Technology Research Institute, Hsinchu (TW)

(72) Inventors: Chi-Ying Lu, Tainan (TW); Jo-Ping Lee, Hsinchu (TW); Hui-Hsin Lu, New Taipei (TW); Ja-Der Liang, New Taipei (TW); Kai-Wen Huang, Taipei (TW); Zong-Yi Hsiao, Nantou County (TW)

(73) Assignee: Industrial Technology Research Institute, Hsinchu (TW)

(*) Notice: Subject to any disclaimer, the term of this patent is extended or adjusted under 35 U.S.C. 154(b) by 423 days.

(21) Appl. No.: 16/231,601

(22) Filed: Dec. 24, 2018

(65) Prior Publication Data

US 2020/0197071 A1 Jun. 25, 2020

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1206* (2013.01); *A61B 2018/00577* (2013.01); *A61B 2018/00791* (2013.01); *A61B 2018/126* (2013.01); *A61B 2018/1253* (2013.01); *A61B 2018/1467* (2013.01)

(58) Field of Classification Search
CPC . A61B 18/1206; A61B 18/14; A61B 18/1477; A61B 2018/00023; A61B 2018/00029; A61B 2018/00577; A61B 2018/00791; A61B 2018/1253; A61B 2018/126; A61B 2018/143; A61B 2018/1467; A61B 2018/1475

See application file for complete search history.

(56) References Cited

U.S. PATENT DOCUMENTS 5,551,426 A * 9/1996 Hummel ................ A61B 5/287
600/374
5,810,804 A 9/1998 Gough et al.
(Continued)

FOREIGN PATENT DOCUMENTS

CN 2925405 7/2007
CN 201879818 6/2011
(Continued)

OTHER PUBLICATIONS

Philippe L. Pereira et al., "Radiofrequency Ablation: In Vivo Comparison of Four Commercially Available Devices in Pig Livers", Radiology, Aug. 2004, pp. 482-490.
(Continued)

*Primary Examiner* — Michael F Peffley
(74) *Attorney, Agent, or Firm* — JCIPRNET

(57) ABSTRACT

An ablation device including a first electrode, at least one second electrode and a guiding sleeve is provided. The guiding sleeve is sleeved outside the first electrode and the second electrode, so as to fold the second electrode. The guiding sleeve is adapted to move along an axial direction of the first electrode, so as to adjust a length of the first electrode exposed by the guiding sleeve and enable the second electrode to be released and expand in a radial direction of the first electrode.

16 Claims, 6 Drawing Sheets

(56) References Cited

U.S. PATENT DOCUMENTS

| | | | |
|---|---|---|---|
| 6,071,280 A * | 6/2000 | Edwards | A61B 18/1477 606/41 |
| 6,090,105 A | 7/2000 | Zepeda et al. | |
| 6,379,353 B1 | 4/2002 | Nichols | |
| 6,454,765 B1 | 9/2002 | Leveen et al. | |
| 6,468,273 B1 * | 10/2002 | Leveen | A61B 18/1477 606/41 |
| 7,160,296 B2 * | 1/2007 | Pearson | A61B 18/1477 606/42 |
| 7,680,543 B2 * | 3/2010 | Azure | A61B 18/1477 607/115 |
| 8,409,195 B2 | 4/2013 | Young | |
| 8,540,710 B2 | 9/2013 | Johnson et al. | |
| 8,734,439 B2 | 5/2014 | Gough et al. | |
| 8,758,339 B2 | 6/2014 | Bee et al. | |
| 8,845,635 B2 * | 9/2014 | Daniel | A61B 18/148 606/50 |
| 2014/0296844 A1 | 10/2014 | Kevin et al. | |
| 2018/0325424 A1 | 11/2018 | Borsic | |

FOREIGN PATENT DOCUMENTS

| | | |
|---|---|---|
| CN | 103519889 | 1/2014 |
| CN | 204106192 | 1/2015 |
| CN | 205126408 | 4/2016 |
| CN | 106264711 | 1/2017 |
| CN | 206167034 | 5/2017 |
| CN | 206424146 | 8/2017 |
| EP | 1576932 | 9/2005 |
| EP | 2851027 | 3/2015 |
| TW | 201703733 | 2/2017 |
| WO | 2016030429 | 3/2016 |

OTHER PUBLICATIONS

Gaia Schiavon et al., "The effect of baseline morphology and its change during treatment on the accuracy of Response Evaluation Criteria in Solid Tumours in assessment of liver metastases", European Journal of Cancer, Jan. 2014, pp. 972-980.

S. Nahum Goldberg, "Radiofrequency tumor ablation: principles and techniques", European Journal of Ultrasound, Jun. 2001, pp. 129-147.

Dieter Haemmerich et al., "Hepatic Radiofrequency Ablation With Internally Cooled Probes: Effect of Coolant Temperature on Lesion Size", IEEE Transactions on Biomedical Engineering, Apr. 2003, pp. 493-500.

Felix Y. Yap et al., "Quantitative morphometric analysis of hepatocellular carcinoma: development of a programmed algorithm and preliminary application", Diagnostic and Interventional Radiology, Mar.-Apr. 2013, pp. 97-105.

Dieter Haemmerich, "Biophysics of Radiofrequency Ablation", Crit Rev Biomed Eng, Jan. 2010, pp. 1-16.

Carlton C. Barnett, Jr. et al., "Ablation Techniques: Ethanol Injection, Cryoablation, and Radiofrequency Ablation", Operative Techniques in General Surgery, Mar. 2002, pp. 65-75.

Muneeb Ahmed et al., "Principles of and Advances in Percutaneous Ablation", Radiology, Feb. 2011, pp. 351-369.

Christopher L. Brace, "Radiofrequency and microwave ablation of the liver, lung, kidney and bone: What are the differences: "Organ-specific thermal ablation"", Curr Probl Diagn Radiol., Sep. 2010, pp. 1-17.

Stephan Clasen et al., "Multipolar Radiofrequency Ablation with Internally Cooled Electrodes: Experimental Study in ex Vivo Bovine Liver with Mathematic Modeling", Radiology, Mar. 2006, pp. 881-890.

Covidien, "Cool-tip RF-ablationssystem, serie E", Covidien, Jan. 2010, pp. 1-128.

"Office Action of China Counterpart Application", dated Oct. 29, 2020, pp. 1-10.

"Office Action of Taiwan Counterpart Application", dated Mar. 11, 2020, p. 1-p. 9.

"Office Action of Taiwan Counterpart Application," dated Aug. 2, 2019, p. 1-p. 9.

"Office Action of Taiwan Counterpart Application," dated Nov. 4, 2019, p. 1-p. 9.

"Office Action of Taiwan Counterpart Application", dated Mar. 20, 2020, p. 1-p. 9.

* cited by examiner

US 11,135,004 B2

ABLATION DEVICE

TECHNICAL FIELD

The disclosure relates to an ablation device, particularly related to an adjustable ablation device.

RELATED ART

Radiofrequency ablation (RFA) is currently the most widely-used technique of tumor ablation. During RFA procedure, under the guidance with a medical imaging tool such as, for example, ultrasound, computed tomography (CT), magnetic resonance imaging (MRI) or the like, a doctor can precisely inserts an ablation device into a treatment area. At this moment, a conductive area of the ablation device emits the radio frequency waves, and due to ionic agitation, tissue around the radio frequency waves generates heat such that the temperature in the treatment area starts to rise up. When the temperature of the treatment area reaches 45° C. or higher, the tissue in the treatment area, which includes tumors, causes the coagulation necrosis of local tissue. An ablation zone of the ablation device is determined by a conduction range of the ablation device. Due to specification limits of the existing products, in the event of a tumor having an irregular shape or larger volume, it is usually necessary to perform multiple ablations and sacrifice normal cell tissue around the treatment area in order to completely ablate the tumor. For these cases, it may take time to perform the procedure.

SUMMARY

An ablation device of the disclosure includes a first electrode, at least one second electrode and a guiding sleeve. The guiding sleeve is sleeved outside the first electrode and the second electrode, so as to fold the second electrode. The guiding sleeve is adapted to move along an axial direction of the first electrode, so as to adjust a length of the first electrode exposed by the guiding sleeve and enable the second electrode to be released and expand along a radial direction of the first electrode.

Several embodiments accompanied with figures are described in detail below to further describe the disclosure in details.

DESCRIPTION OF THE EMBODIMENTS

Figure 1:
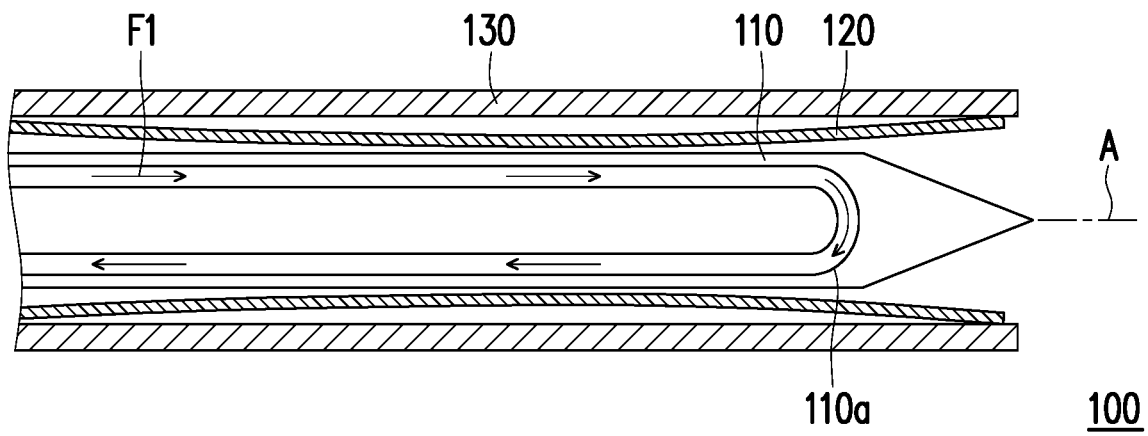
FIG. 1 is a schematic cross-sectional view of an ablation device of an embodiment of the disclosure.
Figure 2:
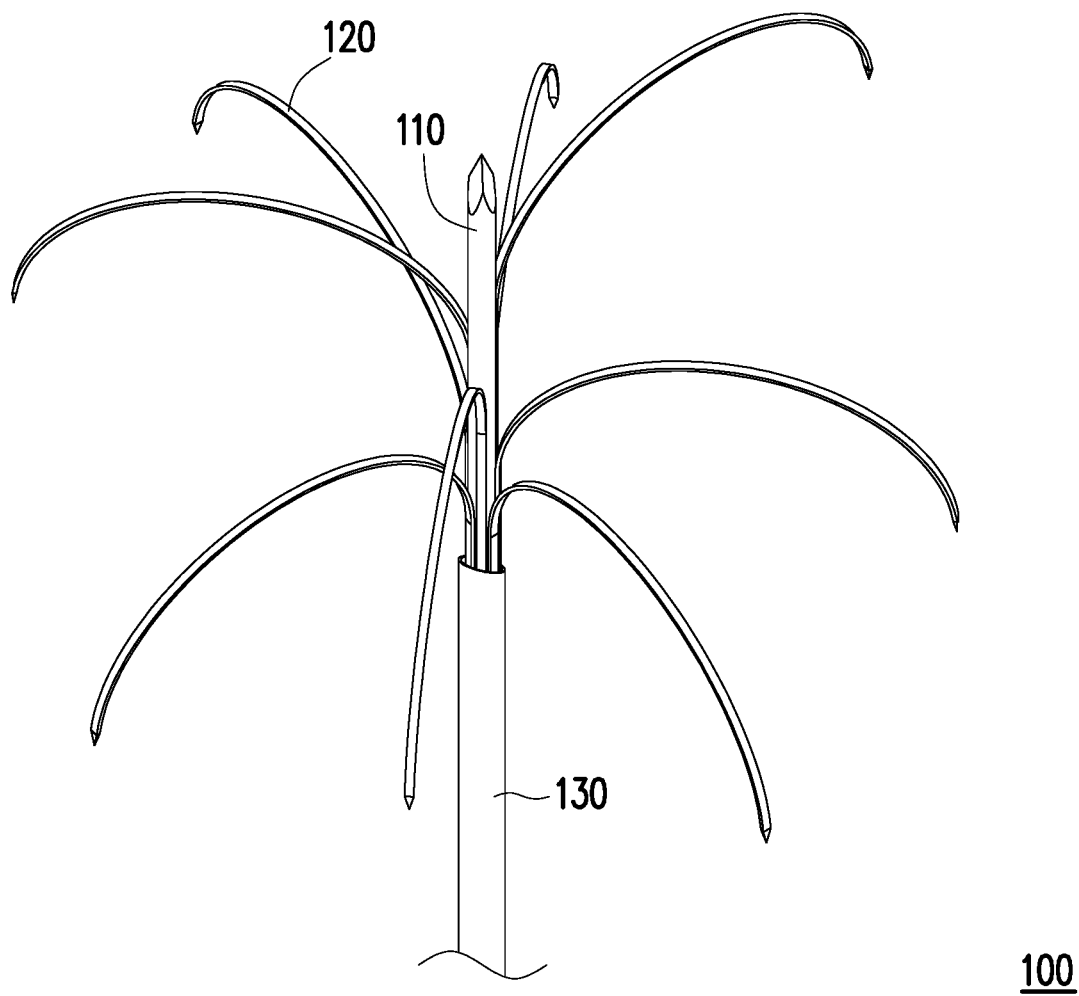
FIG. 2 is a schematic expanded view of a second electrode of FIG. 1.

FIG. 1 is a schematic cross-sectional view of an ablation device of an embodiment of the disclosure. FIG. 2 is a schematic expanded view of a second electrode of FIG. 1. Referring to FIG. 1 and FIG. 2, an ablation device 100 of the embodiment includes a first electrode 110, at least one second electrode 120 (shown as plurality), and a guiding sleeve 130. The first electrode 110 is, for example, needle-shaped or columnar and may be solid or hollow. The second electrodes 120 are disposed outside the first electrode 110 and surround the first electrode 110. Each second electrode 120, for example, is resilient and tends to bend and expand in a radial direction of the first electrode 110. The guiding sleeve 130 includes, for example, a conductive material (e.g., conductive metal) or an insulating material, and is sleeved outside the first electrode 110 and the second electrodes 120, so as to resist elastic force of each second electrode 120 and fold the second electrodes 120 as shown in FIG. 1. The guiding sleeve 130 is movable along an axial direction A of the first electrode 110 to change into a state as shown in FIG. 2, so that a length of the first electrode 110 exposed by the guiding sleeve 130 can be adjusted, and each second electrode 120 can be released and can expand in the radial direction perpendicular to the axial direction A of the first electrode 110.

Based on this configuration, during a surgery, an ablation zone can be adjusted by changing the exposed length of the first electrode 110 along the axial direction A by moving the guiding sleeve 130, so that irregularly-shaped tumors can be conveniently and effectively ablated. In addition, by closing the second electrodes 120 by the guiding sleeve 130, the ablation device 100 can be easily inserted into an affected part. After the ablation device 100 is inserted into the affected part, according to the shape and size of the tumors, each second electrode 120 can be released by the guiding sleeve 130 and can expand at an appropriate position, thereby increasing a radial ablation zone of the ablation device 100 along the axial direction A and effectively ablating the tumors.

Further, the second electrodes 120 are, for example, electrically independent of each other, and each second electrode 120 is individually actuatable and can move along the axial direction A relative to the first electrode 110. In this way, ablation may be sequentially performed by moving the second electrodes 120 at different time points, and ablation may be performed by using different positions of the second electrodes 120 in the axial direction A, such that the radial ablation zone is enhanced with respect to a location requiring treatment, thereby enabling application to adapt to the affected part in various different cases.

In the embodiment, the guiding sleeve 130 may have an outer diameter less than 3 mm to facilitate the insertion into the affected part in the closing state. On the other hand, when the second electrodes 120 expand as shown in FIG. 2 to increase an outer diameter of the ablation device 100 in the radial direction, the maximum outer diameter of the ablation device 100 in the radial direction has an enhanced radial ablation zone. In addition, in the embodiment, a cross section of each second electrode 120 is, for example, flat, such that the second electrode 120 can easily bend in an expected direction. In other embodiments, the cross section may be circular or of other shape, and the disclosure is not limited thereto.

Referring to FIG. 1, the first electrode 110 of the embodiment may have a hollow structure and have a flow channel 110a therein. A cooling fluid F1 is adapted to flow along the flow channel 110a to cool the ablation device 100 and prevent the ablation device 100 from overheating during ablation. In the embodiment, the number of the flow channel 110a is one; however, in other embodiments, the number of flow channels may be plural, and the disclosure is not limited thereto. In other embodiments, the first electrode 110 may have no flow channel disposed therein, or the ablation device 100 may be cooled by other suitable methods.

In the embodiment, the first electrode 110 and the second electrode 120 are, for example, a positive electrode and a negative electrode, respectively, and are arranged in a bipolar configuration. However, the disclosure is not limited thereto. The first electrode 110 and the second electrode 120 may both be positive electrodes or both be negative electrodes, and are arranged in a monopolar configuration. In the bipolar configuration, current is generated between the first electrode 110 and the second electrode 120, and a smaller ablation zone may be achieved. In the monopolar configuration, current is generated between the ablation device 100 and an electrode sheet attached to the vicinity of the affected part, and a larger ablation zone may be achieved. The ablation device 100 may have the bipolar configuration or the monopolar configuration as needed to meet different surgical needs.

Figure 3:
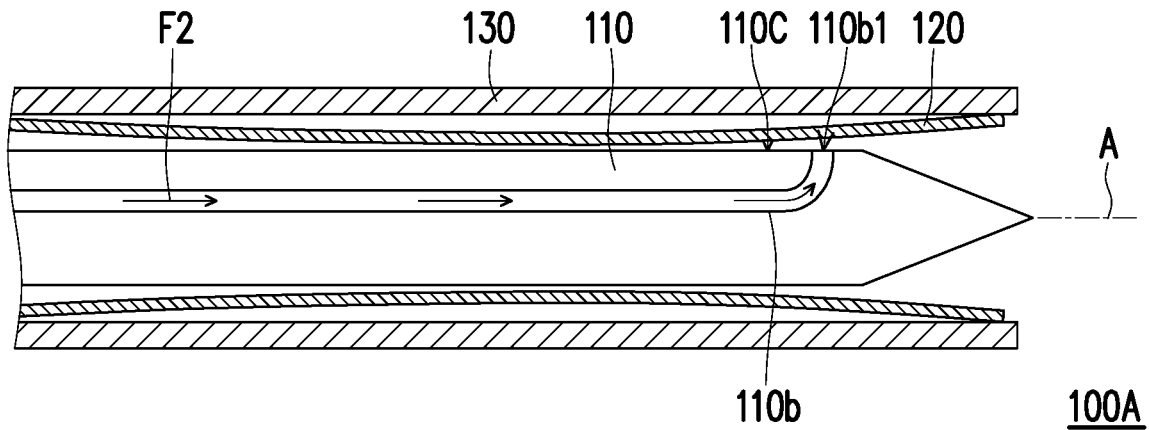
FIG. 3 is a schematic cross-sectional view of an ablation device of another embodiment of the disclosure.

FIG. 3 is a schematic cross-sectional view of an ablation device of another embodiment of the disclosure. An ablation device 100A shown in FIG. 3 is similar to the ablation device 100 shown in FIG. 1. However, it should be noted that in the first electrode 110 of FIG. 3 there is no flow channel for cooling but a flow channel 110b for flowing a working fluid F2. The flow channel 110b has an opening 110b1 on a surface 110c of the first electrode 110, and the working fluid F2 is adapted to flow along the flow channel 110b and to be injected from the opening 110b1 to the affected part. The working fluid F2 may be an agent required for surgery, such as an anesthetic, a developer or the like, or may be saline for enhancing electrical conductivity of tissue. The disclosure is not limited thereto. In the embodiment, the number of the flow channel 110b is one; however, in other embodiments, the number of flow channels may be plural, and the disclosure is not limited thereto.

Figure 4:
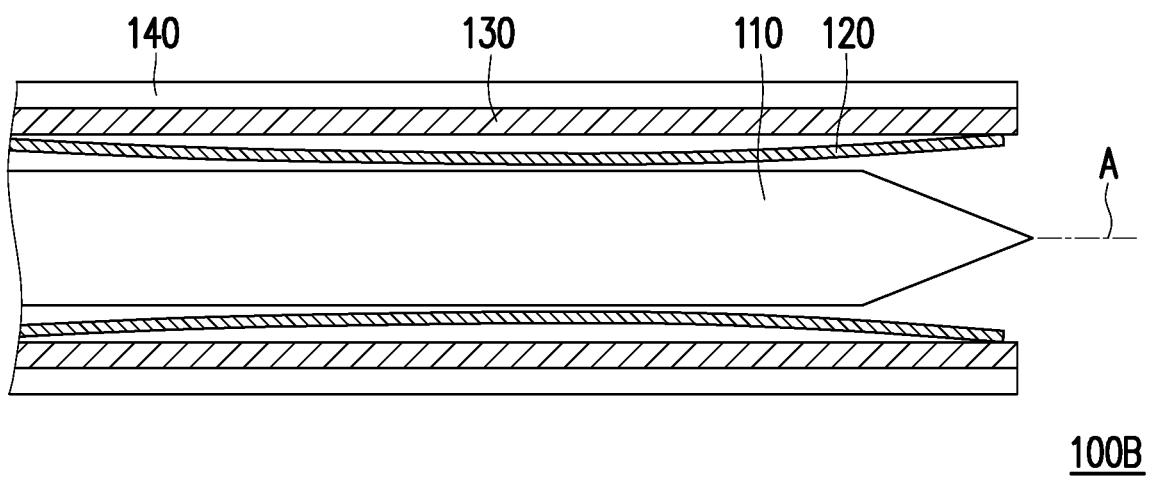
FIG. 4 is a schematic cross-sectional view of an ablation device of another embodiment of the disclosure.

FIG. 4 is a schematic cross-sectional view of an ablation device of another embodiment of the disclosure. An ablation device 100B shown in FIG. 4 is similar to the ablation device 100 shown in FIG. 1. However, it should be noted that a material of the guiding sleeve 130 of the ablation device 100B includes a conductive material (e.g., conductive metal). Accordingly, the ablation device 100B further includes an insulating sleeve 140. The insulating sleeve 140 is sleeved outside the guiding sleeve 130 to prevent the conductive guiding sleeve 130 from unintendedly increasing the ablation zone and also from being electrically conducted to a user's operating end and affecting operation. In the embodiment shown in FIG. 4, the flow channel 110a as shown in FIG. 1 or the flow channel 110b as shown in FIG. 3 may be disposed inside the first electrode 110. The disclosure is not limited thereto.

Figure 5:
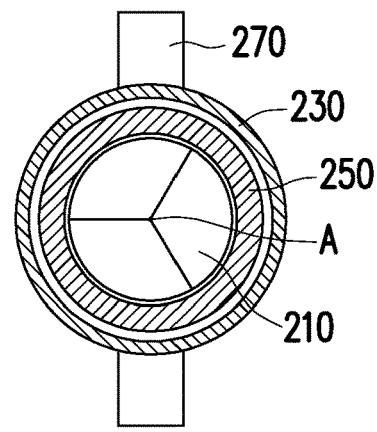
FIG. 5 is a schematic front view of an ablation device of another embodiment of the disclosure.
Figure 6A:
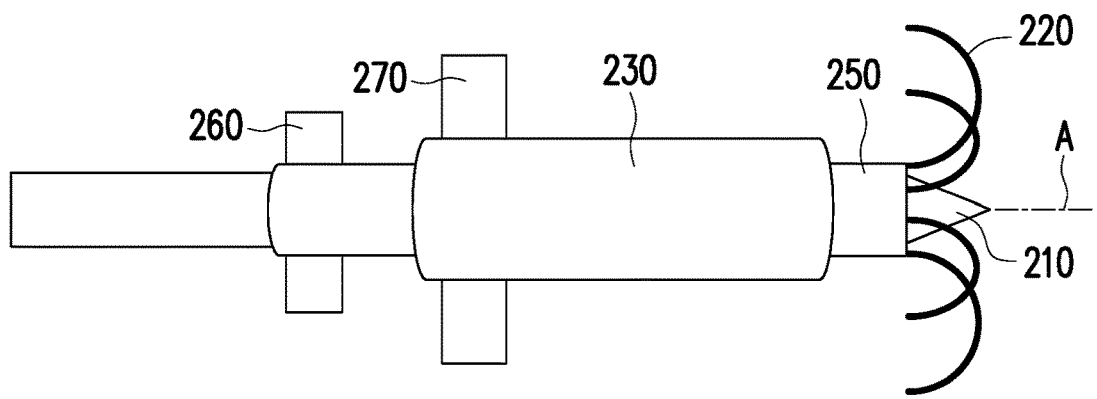
FIG. 6A and FIG. 6B illustrate operation of the ablation device of FIG. 5.
Figure 6B:
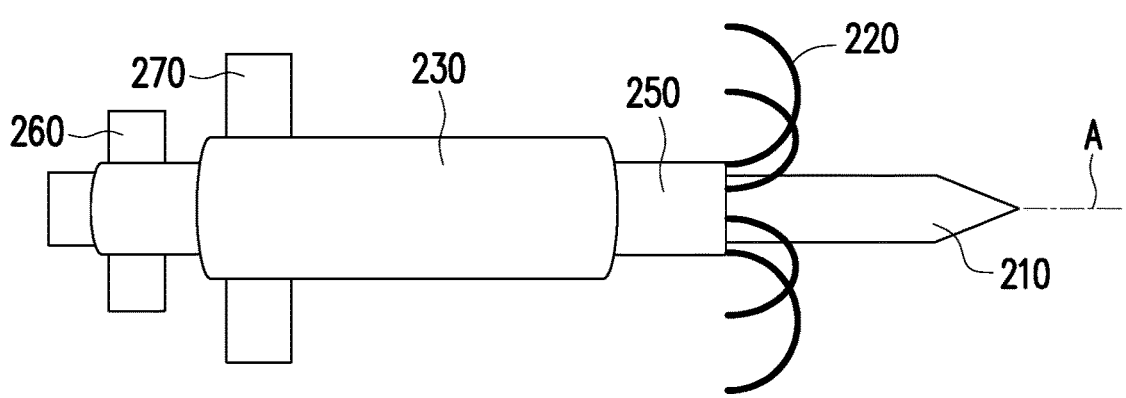

FIG. 5 is a schematic front view of an ablation device of another embodiment of the disclosure. FIG. 6A and FIG. 6B illustrate operation of the ablation device of FIG. 5. For clearer illustration, a second electrode 220 in FIG. 6A and FIG. 6B is not shown in FIG. 5. In an ablation device 200 of FIG. 5, FIG. 6A and FIG. 6B, a first electrode 210, the second electrode 220, and a guiding sleeve 230 are configured and act similarly as the first electrode 110, the second electrode 120, and the guiding sleeve 130, respectively, of FIG. 1, and explanation thereof will not be repeated. It should be noted that the ablation device 200 further includes a moving member 250. The moving member 250 is disposed outside the first electrode 210 and adapted to move along the axial direction A of the first electrode 210. A plurality of second electrodes 220 are configured to be connected to one end of the moving member 250. Accordingly, by movement of the moving member 250 along the axial direction A, the second electrodes 220 connected to the moving member 250 can be driven to move along the axial direction A.

In addition, the ablation device 200 further includes an operating member 260. The operating member 260 is connected to one end of the moving member 220 away from the second electrodes 220, and is adapted to receive a force to drive the moving member 220 and the second electrodes 220 correspondingly configured to be connected to the moving member 220 to move along the axial direction A. Similarly, the ablation device 200 further includes an operating member 270 connected to the guiding sleeve 210 and adapted to receive a force to drive the guiding sleeve 270 to move along the axial direction A. Accordingly, the user may pull or push the operating member 260 and the operating member 270 to adjust relative positions of the first electrode 210, the guiding sleeve 230 and the moving member 250 as needed as shown in FIG. 6A and FIG. 6B.

Figure 7:
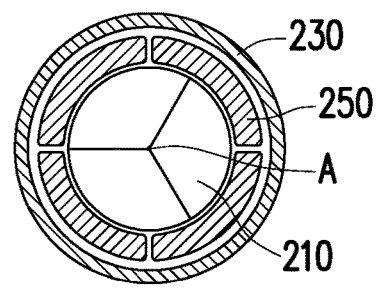
FIG. 7 is a schematic front view of an ablation device of another embodiment of the disclosure.
Figure 8:
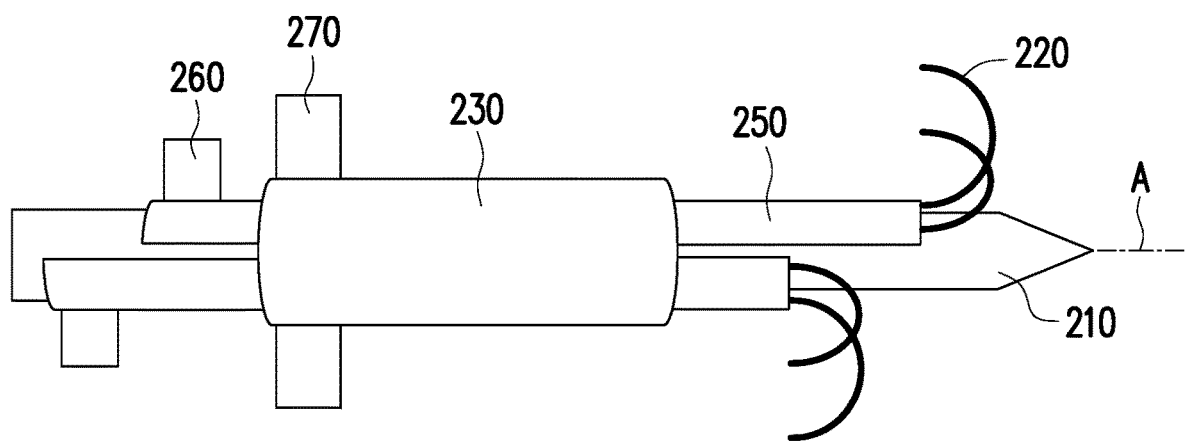
FIG. 8 illustrates operation of the ablation device of FIG. 7.

FIG. 7 is a schematic front view of an ablation device of another embodiment of the disclosure. FIG. 8 illustrates operation of the ablation device of FIG. 7. For clearer illustration, the second electrode 220 in FIG. 8 is not shown in FIG. 7. An ablation device 200A of FIG. 7 and FIG. 8 is similar to the ablation device 200 of FIG. 5, FIG. 6A and FIG. 6B. However, it should be noted that the number of the moving member 250 of the ablation device 200A is plural (shown as four in FIG. 7), and each moving member 250 is connected to some of the second electrodes 220. Moreover, the moving members 250 are electrically independent of each other. Accordingly, each moving member 250 is individually actuatable and can move along the axial direction A relative to the first electrode 210. Thus, ablation may be sequentially performed at different time points by using the moving members 250 and the second electrodes 220 correspondingly and respectively connected to the different moving members 250, and ablation may be performed by using the moving members 250 and the second electrodes 220 correspondingly and respectively connected to the different moving members 250 for ablation at different positions in the axial direction A, such that the radial ablation zone is enhanced with respect to a location requiring treatment, to adapt to the affected parts in various different situations. In other embodiments, other numbers of moving members 250 may be provided, and the disclosure is not limited thereto. Examples are provided and explained below with reference to drawings.

Figure 9:
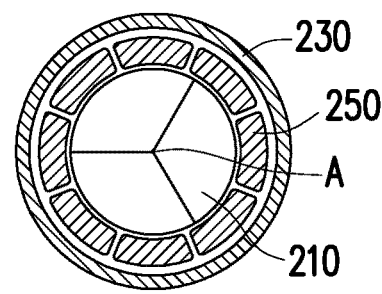
FIG. 9 is a schematic front view of an ablation device of another embodiment of the disclosure.
Figure 10:
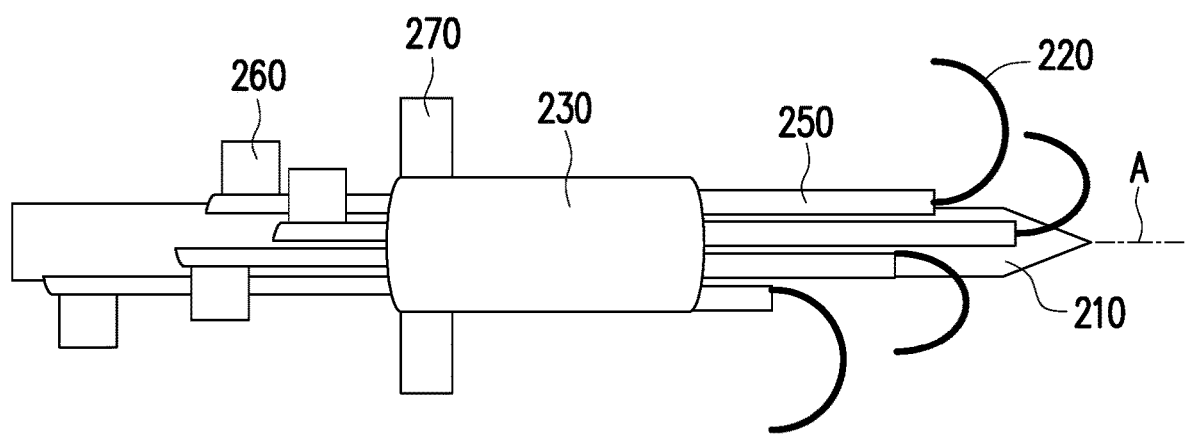
FIG. 10 illustrates operation of the ablation device of FIG. 9.

FIG. 9 is a schematic front view of an ablation device of another embodiment of the disclosure. FIG. 10 illustrates operation of the ablation device of FIG. 9. For clearer illustration, the second electrode 220 in FIG. 10 is not shown in FIG. 9. An ablation device 200B of FIG. 9 and FIG. 10 is similar to the ablation device 200A of FIG. 7 and FIG. 8. However, it should be noted that the number of the moving member 250 of the ablation device 200B is eight. In other embodiments, the number of the moving member 250 may be two, three or five, etc., and the disclosure is not limited thereto. In addition, in the embodiment, the number of the second electrode 220 correspondingly disposed on each moving member 250 may be one. However, in other embodiments, the number of the second electrode 220 on each moving member 250 may be plural, and the disclosure is not limited thereto.

Figure 11:
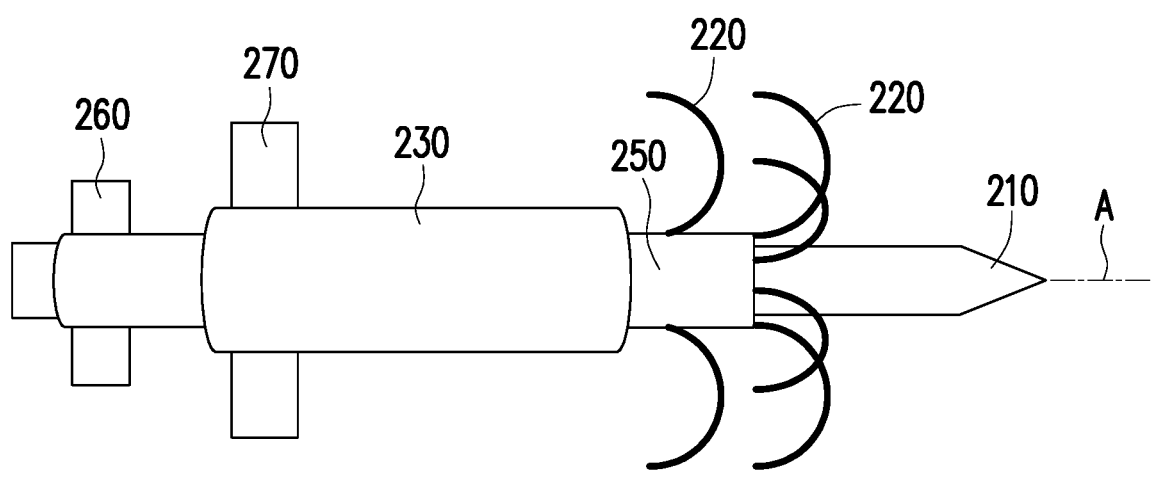
FIG. 11 is a schematic view of an ablation device of another embodiment of the disclosure.

FIG. 11 is a schematic view of an ablation device of another embodiment of the disclosure. An ablation device 200C of FIG. 11 is similar to the ablation device 200 of FIG. 5, FIG. 6A and FIG. 6B. However, it should be noted that, while a plurality of second electrodes 220 are configured to be connected to the moving member 250, some of the second electrodes 220 are arranged and connected to the moving member 250 along the axial direction A, instead of being disposed only at one end of the moving member 250, thereby increasing the ablation zone of the second electrodes 220 perpendicular to the axial direction A. In the embodiments shown in FIG. 7 to FIG. 10, a plurality of second electrodes 220 arranged along the axial direction A may be disposed on each moving member 250, and the disclosure is not limited thereto. In addition, in the embodiments shown in FIG. 5 to FIG. 11, the flow channel 110a as shown in FIG. 1 or the flow channel 110b as shown in FIG. 3 may be disposed inside the first electrode 210. The disclosure is not limited thereto.

In the above embodiments, examples are explained in which the second electrode 120 or 220 is disposed outside the first electrode 110 or 210. However, in other embodiments, the first electrode 110 or 210 may be designed to have a hollow structure, and the second electrode 120 or 220 may be disposed inside the first electrode 110 or 210. The disclosure is not limited thereto.

In summary, in the ablation device of the disclosure, the guiding sleeve may be moved during surgery to change the ablation zone of the first electrode along the axial direction, so as to conveniently and effectively ablate tumors. In addition, by closing the second electrode by the guiding sleeve, the ablation device can be easily inserted into an affected part. After the ablation device is inserted into the affected part, according to the shape and size of the tumors, each second electrode can be released by the guiding sleeve and can expand at an appropriate position. Accordingly, the ablation zone of the first electrode along the radial direction can be changed and the tumors having an irregular shape can be effectively ablated. In addition, ablation may be sequentially performed by using a plurality of second electrodes at different time points, and ablation may be performed by using the second electrodes at different positions in the axial direction to adapt to the affected part in various different situations.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An ablation device comprising:
   a first electrode;
   at least one second electrode;
   a guiding sleeve sleeved outside the first electrode and the at least one second electrode to fold the at least one second electrode, wherein the guiding sleeve is adapted to move along an axial direction of the first electrode to adjust a length of the first electrode exposed by the guiding sleeve, and to enable the at least one second electrode to be released and expand in a radial direction of the first electrode, and
   at least one moving member, wherein the at least one moving member is disposed outside the first electrode and is adapted to move along the axial direction of the first electrode, a number of the at least one second electrode is plural, and at least some of the plurality of second electrodes are connected to one end of the at least one moving member.

2. The ablation device according to claim 1, wherein a number of the at least one second electrode is plural, the plurality of second electrodes surround the first electrode, and each of the plurality of second electrodes is adapted to move along the axial direction relative to the first electrode.

3. The ablation device according to claim 2, wherein the plurality of second electrodes are electrically independent of each other.

4. The ablation device according to claim 1, further comprising at least one operating member, wherein the at least one operating member is connected to one end of the at least one moving member away from the plurality of second electrodes, and is adapted to receive a force to drive the at least one moving member and the plurality of second electrodes correspondingly connected to the at least one moving member to move along the axial direction of the first electrode.

5. The ablation device according to claim 1, wherein a number of the at least one moving member is plural, and each of the moving members is connected to some of the plurality of second electrodes.

6. The ablation device according to claim 5, wherein the plurality of moving members are electrically independent of each other.

7. The ablation device according to claim 1, wherein the at least some of the plurality of second electrodes on the at least one moving member are arranged and connected to the at least one moving member along the axial direction of the first electrode.

8. The ablation device according to claim 1, further comprising an operating member, wherein the operating member is connected to the guiding sleeve and adapted to receive a force to drive the guiding sleeve to move along the axial direction of the first electrode.

9. The ablation device according to claim 1, further comprising an insulating sleeve, wherein a material of the guiding sleeve comprises a conductive material, and the insulating sleeve is sleeved outside the guiding sleeve.

10. The ablation device according to claim 1, wherein the guiding sleeve has an outer diameter less than 3 mm.

11. The ablation device according to claim 1, wherein the first electrode has at least one flow channel therein, and a cooling fluid is adapted to flow along the at least one flow channel.

12. The ablation device according to claim 1, wherein the first electrode has at least one flow channel therein, the at least one flow channel has an opening on a surface of the first electrode, and a working fluid is adapted to flow along the at least one flow channel and to be injected from the opening.

13. The ablation device according to claim 1, wherein one of the first electrode and the at least one second electrode is a positive electrode, and the other of the first electrode and the at least one second electrode is a negative electrode.

14. The ablation device according to claim 1, wherein the first electrode and the at least one second electrode are both positive electrodes or are both negative electrodes.

15. The ablation device according to claim 1, wherein the at least one second electrode is disposed outside the first electrode.

16. The ablation device according to claim 1, wherein the at least one second electrode is disposed inside the first electrode.

\* \* \* \* \*